(12) United States Patent
Eiland et al.

(10) Patent No.: US 11,628,256 B2
(45) Date of Patent: Apr. 18, 2023

(54) PLUNGER SUB-ASSEMBLY FOR A PREFILLED MEDICAMENT INJECTOR, A PREFILLED MEDICAMENT INJECTOR AND METHOD FOR ASSEMBLING A PREFILLED MEDICAL INJECTOR

(71) Applicant: Novo Nordisk A/S, Bagsvaerd (DK)

(72) Inventors: Jacob Eiland, Virum (DK); Frederik Holten-Tingleff, Vaerloese (DK); Peter Bjerrum, Hjallerup (DK); Jonas Moerkeberg Torry-Smith, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 960 days.

(21) Appl. No.: 16/473,833

(22) PCT Filed: Dec. 29, 2017

(86) PCT No.: PCT/EP2017/084856
§ 371 (c)(1),
(2) Date: Jun. 26, 2019

(87) PCT Pub. No.: WO2018/122394
PCT Pub. Date: Jul. 5, 2018

(65) Prior Publication Data
US 2019/0336686 A1 Nov. 7, 2019

(30) Foreign Application Priority Data
Dec. 31, 2016 (EP) .................... 16207660

(51) Int. Cl.
*A61M 5/20* (2006.01)
*A61M 5/315* (2006.01)
*A61M 5/24* (2006.01)

(52) U.S. Cl.
CPC ............ *A61M 5/2033* (2013.01); *A61M 5/24* (2013.01); *A61M 5/31505* (2013.01);
(Continued)

(58) Field of Classification Search
CPC ............ A61M 5/2033; A61M 5/31505; A61M 5/31538; A61M 5/31556; A61M 5/31563;
(Continued)

(56) References Cited

U.S. PATENT DOCUMENTS 5,540,664 A 7/1996 Wyrick
5,695,472 A * 12/1997 Wyrick ............. A61M 5/31595
604/211

(Continued)

FOREIGN PATENT DOCUMENTS

CN 1466472 A 1/2004
CN 105188807 A 12/2015
(Continued)

*Primary Examiner* — Nathan R Price
*Assistant Examiner* — Anh Bui
(74) *Attorney, Agent, or Firm* — Wesley Nicolas

(57) ABSTRACT

A plunger sub-assembly (40, 60, 70; 80) for a pre-filled medicament injector for expelling a dose of a medicament, comprising: a) a container (60) holding a medicament, the container (60) comprising a body (61) with a proximally facing rim surface (64), and a distally slideable piston (63); b) a plunger (40); and c) a tolerance compensating element (70; 80) configured to cooperate with the plunger (40) and to cooperate with either the proximally facing rim surface (64) or the piston (63), the tolerance compensating element (70; 80) being rotatable relative to the plunger (40) to adjust the piston (63) end of dose position. The plunger sub-assembly (40, 60, 70; 80) is formed so that end of dose state occurs by the plunger (40) cooperating with the proximally facing rim surface (64). Pre-filled medicament injectors and methods of assembling a pre-filled medicament injector are further described.

16 Claims, 6 Drawing Sheets

(52) U.S. Cl.
CPC .... *A61M 5/31511* (2013.01); *A61M 5/31538* (2013.01); *A61M 5/31551* (2013.01); *A61M 5/31556* (2013.01); *A61M 5/31563* (2013.01); *A61M 2005/3154* (2013.01); *A61M 2005/31508* (2013.01)

(58) Field of Classification Search
CPC ............... A61M 5/24; A61M 5/31551; A61M 5/31511; A61M 2005/31508; A61M 2005/3154
See application file for complete search history.

(56) References Cited

U.S. PATENT DOCUMENTS

| | | | |
|---|---|---|---|
| 6,562,007 B1 * | 5/2003 | Falsey | ............... A61M 5/31551 604/211 |
| 10,357,617 B2 | 7/2019 | Holmqvist | |
| 2002/0173752 A1 | 11/2002 | Polzin | |
| 2013/0023831 A1 | 1/2013 | Helmer et al. | |

FOREIGN PATENT DOCUMENTS

| | | | |
|---|---|---|---|
| EP | 1324794 | A2 | 7/2003 |
| JP | H4502877 | A | 5/1992 |
| JP | H8507239 | A | 8/1996 |
| WO | 2011121061 | A1 | 10/2011 |
| WO | 2016075254 | A1 | 5/2016 |

\* cited by examiner

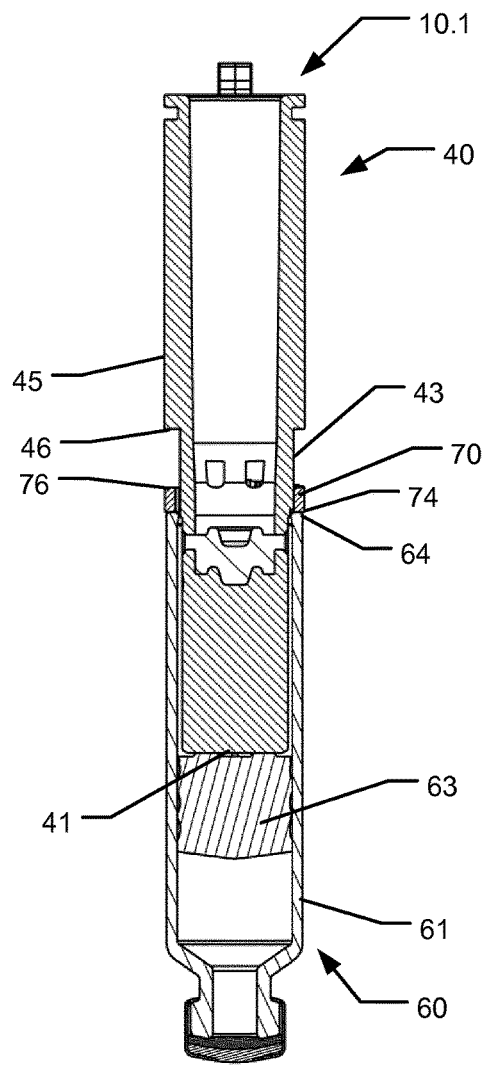
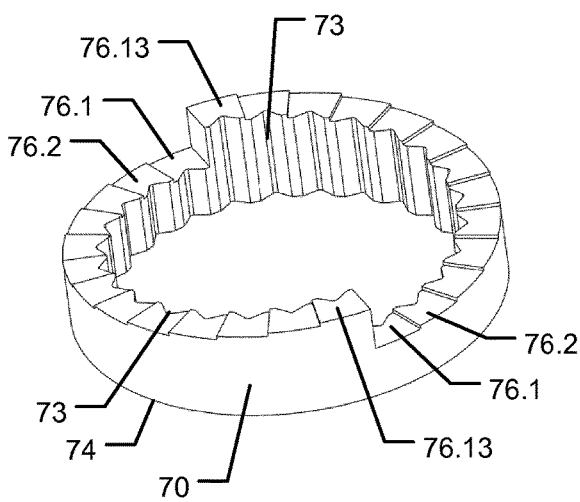
Fig. 3
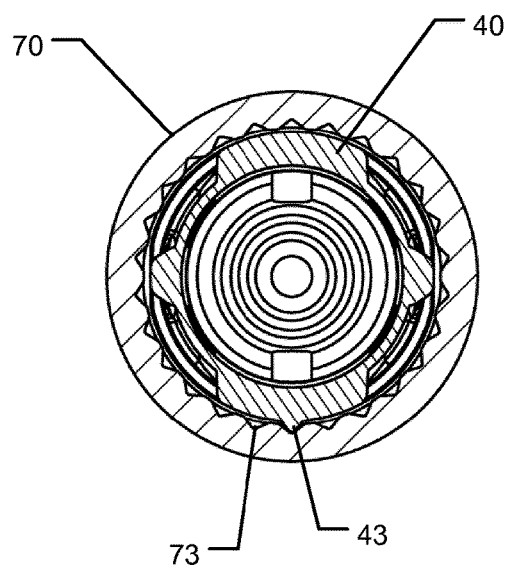
Fig. 4
Fig. 2

PLUNGER SUB-ASSEMBLY FOR A PREFILLED MEDICAMENT INJECTOR, A PREFILLED MEDICAMENT INJECTOR AND METHOD FOR ASSEMBLING A PREFILLED MEDICAL INJECTOR

CROSS-REFERENCE TO RELATED APPLICATIONS

This application is a 35 U.S.C. § 371 National Stage application of International Application PCT/EP2017/084856 (published as WO 2018/122394), filed Dec. 29, 2017, which claims priority to European Patent Application 16207660.8, filed Dec. 31, 2016, the contents of all above-named applications are incorporated herein by reference.

The present invention relates to an assembly of components for a medicament injector that allows for accurately dosing of a medicament from a cartridge. In particular, the present invention relates to a plunger sub-assembly for a prefilled medicament injector and a method of assembling such pre-filled medicament injector.

BACKGROUND

In relation to some diseases patients must inject a medicament on a regular basis such as once weekly, once daily or even a plurality of times each day. In order to help patients overcome fear of needles, fully automatic injection devices have been developed with the aim of making the use of the injection device as simple as possible. Auto-injectors typically include a container in the form of a cartridge or a syringe that is accommodated within a housing. Prefilled auto-injectors that are intended for single use have been developed to provide particularly simple and user-friendly devices. An example of such autoinjector is disclosed in WO 2016/075254 A1.

WO 2011/121061 discloses a piston rod assembly for a drug delivery device allowing for multiple dosing of a required dosage by respective dose setting and expelling operations. For the purpose of tolerance elimination the piston rod assembly comprises an adjusting member arranged between the piston and the piston rod. The adjusting member is threadedly engaged with the piston rod in order to axially displace the piston rod and the adjusting member relative to each other to ensure mutual abutment between the piston and the piston rod.

U.S. Pat. No. 5,695,472 further discloses a modular fluid medication injection assembly. By disassembling the device, a user may prepare the device for the expelling of a first dose or prepare the device for expelling of subsequent doses. To enable use of different kinds of medication for the device, a user may manually adjust for variations in the length of a syringe of the device. Multiple components are used to enable variability of dose setting and the manual adjustment is not suitable to adjust for tolerance variations.

The filling of medicament containers, such as septum-equipped cartridges, is impacted by the manufacturing of the container. For e.g. a glass cartridge, the dimensions of the cartridge combined with the filling technique typically results in minor inaccuracies of the total volume contained by the cartridge. Delivering a drug in a well-defined volume is essential for many therapies, e.g. treatment of diabetes.

For some medical applications prefilled medicament injectors that are intended for single use administration, such as pre-filled auto-injectors, do not meet the requirements having regard to dosage accuracy. Hence, in certain therapeutic areas there is a need for improved pre-filled medicament injectors.

SUMMARY

It is an object of the present invention to provide a medicament injector featuring improved dosage accuracy. It is a further object of the invention to provide a simplified and robust method of manufacturing such medicament injector. Finally, it is an object of the invention to provide an improved plunger assembly to be used in medicament injectors.

In the disclosure of the present invention, embodiments and aspects will be described which will address one or more of the above objects or which will address objects apparent from the below disclosure as well as from the description of exemplary embodiments.

In a first aspect, the present invention relates to a plunger sub-assembly for a pre-filled medicament injector for expelling a dose of a medicament, comprising:
  a container holding a medicament, the container comprising a cylindrical container body extending along a central axis between a medicament expelling distal end and a proximal end, wherein an axially slideable piston is arranged within the container body to seal the container proximally, and wherein the proximal end of the container body comprises a proximally facing rim surface,
  a plunger arranged along the axis and configured for driving the piston distally relative to the proximally facing rim surface, the plunger being distally movable from a start position where the plunger is not cooperating with the proximally facing rim surface until an end position relative to the container where the plunger cooperates with the proximally facing rim surface thereby preventing the plunger from moving further distally, the piston assuming an end of dose position relative to the proximally facing rim surface when the plunger assumes the end position, and
  an adjustable blocking means associated with the plunger and the container to provide an axial blocking means for the plunger in the end position,
  wherein the adjustable blocking means comprises a tolerance compensating element configured to cooperate with the plunger and to cooperate with either the proximally facing rim surface or the piston, wherein the tolerance compensating element is rotatable relative to the plunger to adjust the piston end of dose position relative to the proximally facing rim surface, and
  wherein the tolerance compensating element is so configured that, when the plunger assumes the end position, either
    a) the plunger engages directly with the piston, whereas the tolerance compensating element directly engages both the plunger and the proximally facing rim surface, or
    b) the plunger directly engages with the proximally facing rim surface, whereas the tolerance compensating element directly engages both the plunger and the piston.

Due to the plunger sub-assembly includes a mechanism where axial length compensation of the plunger and the tolerance compensating element is performed by performing a relative rotational movement or rotational alignment between the tolerance compensating element and the plunger, and due to the plunger-assembly includes a stop surface to cooperate with the proximally facing rim surface of the container body, a particular simple way of obtaining tolerance compensation is obtained. Thereby, the accuracy of the amount of expelled dosages across different samples in a series of pre-filled medicament injectors can be obtained.

In accordance with the present invention, in large scale manufacturing, the tolerance compensation can be performed on the basis of simple measurements and simple tolerance compensation adjustments, which all can be carried out by automated means.

With the container in a pre-expelling state, a proximally facing surface of the piston assumes an axial start position relative to the proximally facing rim surface of the container body. The said axial start position can be easily determined or estimated and the plunger sub-assembly is adjusted so that, when built into a medicament injector, the expelling mechanism moves the plunger distally to perform an expelling movement for moving the piston of the container in an expelling stroke of high accuracy.

In some embodiments, the plunger sub-assembly is so configured that, at least when the plunger assumes the end position, a distally facing geometry of the plunger engages directly with the piston, whereas the tolerance compensating element directly engages both the plunger and the proximally facing rim surface.

The tolerance compensating element may in some embodiments be formed as a collar arranged circumferentially relative to the plunger and having a distal annular surface that is configured for engaging the proximally facing rim surface of the container body. The collar may be formed to either partially of fully circumscribe the plunger.

In further embodiments one of the plunger and the tolerance compensating element comprises a contour system comprising a plurality of circumferentially disposed stop surfaces that are arranged axially offset relative to each other, and wherein the other of the plunger and the tolerance compensating element comprises a counter stop surface arranged to axially engage a selective one of the plurality of circumferentially stop surfaces. When in an initial assembly configuration, the tolerance compensating element and the plunger are selectively positionable or positioned relative to each other to rotationally align the counter stop surface with a selective one of the plurality of circumferentially disposed stop surfaces to thereby adjustably control the end position of the plunger relative to the container, enabling the counter stop surface to axially abut the selected one of the plurality of circumferentially disposed stop surfaces.

The plurality of circumferentially disposed stop surfaces of the contour system may be formed to define a plurality of steps that are circumferentially arranged and axially offset relative to one another.

In some embodiments, instead of forming a stepped configuration, the plurality of circumferentially disposed stop surfaces of the contour system are provided as contiguously formed stop surfaces that together form at least one continuous rib extending helically around the central axis.

In a final assembly configuration of the plunger sub-assembly, such as prior to insertion of the plunger assembly into the housing of a medicament injector, or as delivered to the customer, the tolerance compensating element and the plunger are positioned rotationally locked relative to each other with rotational alignment of the counter stop surface with the selected one of the plurality of circumferentially disposed stop surfaces. Hence, when the plunger of the plunger-assembly has been moved fully distally relative to the container barrel, e.g. when the medicament injector has expelled the intended dose, said counter stop surface is in axially abutment with said selected one of the plurality of circumferentially disposed stop surfaces to thereby control the end position of the plunger relative to the container body.

In some embodiments, the plunger and the tolerance compensating element engage with each other by means of a tongue and groove system. The tongue and groove system may be formed to define at least one tongue and a plurality of axially extending grooves disposed in a coaxial configuration, i.e. where the at least one tongue is arranged on one of the plunger and the tolerance compensating element, and the a plurality of axially extending grooves are arranged on the other of the plunger and the tolerance compensating element. The tongue is positionable or positioned in a selective one of said plurality of axially extending grooves to rotationally align said counter stop surface with the selected one of the plurality of circumferentially disposed stop surfaces enabling an axially sliding movement of the plunger and the tolerance compensating element relative to each other while, when the plunger sub-assembly assumes a final assembled state, preventing relative rotational movement there between.

In other embodiments, wherein the plunger sub-assembly may comprise a base component that is mounted axially fixed relative to the container body, wherein the base component partially or fully encircles the plunger, and wherein the plunger and the base component are mounted non-rotatably relative to each other. In such assembly, the base component and the tolerance compensating element may be formed to engage with each other by means of a tongue and groove system, the tongue and groove system defining at least one tongue and a plurality of axially extending grooves disposed in a coaxial configuration, i.e. where the at least one tongue is arranged on one of the base component and the tolerance compensating element, and the a plurality of axially extending grooves are arranged on the other of the base component and the tolerance compensating element. The tongue is positionable or positioned in a selective one of said plurality of axially extending grooves to rotationally align said counter stop surface with the selected one of the plurality of circumferentially disposed stop surfaces to prevent relative rotation between the base component and the tolerance compensating element.

In some embodiments, the counter stop surface and additional corresponding counter stop surfaces are provided as a plurality of circumferentially disposed counter stop surfaces. These may be distributed regularly around the central axis. The respective ones of the plurality of circumferentially disposed counter stop surfaces are configured for simultaneously axially engaging a respective one of the plurality of circumferentially disposed stop surfaces.

The said system of cooperating grooves and tongue may be formed to comprise engaging surfaces being so configured that the tolerance compensating element and the plunger, or the base component, is selectively rotationally positionable relative to each other in incremental angular steps having a step size between 5 and 180 Deg., preferably between 10 and 30 Deg.

In some embodiments, the groove and tongue surfaces are so configured that the tolerance compensating element and the plunger are selectively rotationally positionable relative to each other in incremental angular steps having a step size of 180 Deg.

The plunger and the tolerance compensating element, when assuming a final assembly configuration, are prevented from rotating relative to each other by means of a rotational lock. Said lock may be formed by cooperating rigid geometries, or by a rotational detent mechanism.

In some embodiments, the groove and tongue surfaces comprise at least one resiliently biased tongue surface exclusively enabling rotational movement between the tolerance compensating element and the plunger, or the base component, upon exertion of torque exceeding a predetermined magnitude acting for relative rotation between the tolerance compensating element and the plunger.

In other alternative embodiments, the plunger sub-assembly is configured so that the tolerance compensating element is arranged axially between the plunger and the piston of the container. The tolerance compensating element comprises a distally facing surface configured to directly engage with the piston. The plunger defines a fixed stop surface configured to directly engage the proximally facing rim surface when the plunger assumes the end position. The tolerance compensating element includes a thread that is in threaded engagement with a thread on the plunger, the threaded engagement being configured to enable adjustment of the axial distance between the tolerance compensating element and the fixed stop surface and configured to inhibit rotational movement between the plunger and the tolerance compensating element when an axial force exerted by the plunger acts on the piston to drive the piston distally. Said threaded engagement may be configured as a self-locking threaded engagement. Alternatively, a rotational detent mechanism is provided alongside with the threaded engagement.

In some embodiments, the container of the plunger sub-assembly defines a cartridge that comprises a septum that seals an expelling distal end of the container body, the septum being penetrable by a needle cannula to establish fluid communication with the interior of the container. In alternative embodiments, the container forms a syringe having a needle attached to the container body. In particular embodiments, the container body is provided as a tubular glass barrel.

In a second aspect, the present invention relates to a pre-filled medicament injector for expelling a dose of a medicament, comprising:
  a housing comprising first and second housing components,
  a plunger sub-assembly as defined in accordance with the first aspect, and
  an expelling mechanism comprising an actuator configured for, upon activation, exerting a distally directed force on the plunger for expelling the dose of the medicament,
  wherein the plunger sub-assembly and the expelling mechanism are accommodated non-removably relative to the first and second housing components.

In some embodiments, the tolerance compensating element and the plunger are positioned relative to each other providing a permanent rotational alignment between the counter stop surface and a selected one of the circumferentially disposed stop surfaces, enabling said counter stop surface to axially abut said selected one of the circumferentially disposed stop surfaces to thereby control the end position of the plunger relative to the container.

In some embodiments, the tolerance compensating element is configured to remain in abutment with the proximally facing rim surface as the plunger moves distally expelling of the dose.

In alternative embodiments, the tolerance compensating element is configured to travel with the plunger as the plunger moves distally when the plunger drives the piston distally.

In some embodiments, the plunger is prevented from rotating relative to the housing of the device.

In some embodiments, the expelling mechanism may comprise an energy source, such as a pre-stressed spring, configured for providing said distally directed force on the plunger upon, e.g. upon activation of the expelling mechanism.

In particular embodiments, the pre-filled medicament injector is so configured that the expelling mechanism exclusively allows for a single activation for expelling a single dose of medicament from the container. As the container may be accommodated irreplaceably within the housing of the injector so that the container cannot be replaced, the pre-filled medicament injector is therefore to be discarded after a single administration.

In a third aspect, the invention relates to a method of assembling a pre-filled medicament injector in accordance with the second aspect described above.

In embodiments where the plunger sub-assembly comprises a plurality of circumferentially disposed stop surfaces as described above, the method comprises the steps of:
  a) providing the container,
  b) determining the axial position ($X_1$) of a proximal face of the piston with respect to the proximally facing rim surface,
  c) establishing a target axial end of dose position ($X_2$) of the proximal face of the piston with respect to the proximally facing rim surface for obtaining a predetermined target axial stroke ($X_S$) for the piston,
  d) providing the plunger and the tolerance compensating element,
  e) based on the target axial end of dose position ($X_2$) of the proximal face of the piston, determining a target axial end position for the distal end face of the plunger,
  f) based on said target axial end position for the distal end face of the plunger, determining a target stop surface selected from the plurality of circumferentially disposed stop surfaces so that the axial end position of the distal end face of the plunger substantially corresponds to the target axial end of dose position ($X_2$) of the proximal face of the piston when said target stop surface axially abuts the counter stop surface,
  g) based on the target stop surface, positioning the plunger and the tolerance compensating element with respect to each other so that the target stop surface rotationally aligns with the counter stop surface,
  h) forming the plunger sub-assembly,
  i) providing the expelling mechanism and the first and second housing components, and
  j) permanently attaching the first and the second housing components to each other to form a housing, whereby the plunger sub-assembly and the expelling mechanism are accommodated non-removable relative to the housing.

In embodiments where the plunger sub-assembly comprises a threaded engagement between the plunger and the tolerance compensating element as described above, the method comprises the steps of:
  a) providing the container,
  b) determining the initial axial position ($X_1$) of the proximal face of the piston with respect to the proximally facing rim surface,
  c) establishing a target axial end of dose position ($X_2$) of the proximal face of the piston with respect to the proximally facing rim surface for obtaining a predetermined target axial stroke ($X_S$) for the piston,
  d) providing the plunger and the tolerance compensating element,
  e) based on the target axial end of dose position ($X_2$) of the proximal face of the piston, determining a target axial distance between the distal end face of the tolerance compensating element and the fixed stop surface of the plunger, f) adjusting the rotational position between the plunger and the tolerance compensating element so that the distal end face of the tolerance compensating element is located said target axial distance from the fixed stop surface of the plunger, g) forming the plunger sub-assembly, h) providing the expelling mechanism and the first and second housing components, and i) permanently attaching the first and the second housing components to each other to form a housing, whereby the plunger sub-assembly and the expelling mechanism are accommodated non-removable relative to the housing.

Finally, in a fourth aspect, the present invention relates to a pre-filled medicament injector for expelling a dose of a medicament, comprising:

a housing, a container holding a medicament and arranged within the housing, the container comprising a cylindrical container body extending along a central axis between a medicament expelling distal end and a proximal end wherein the proximal end defines a proximally facing rim surface, wherein an axially slideable piston is arranged within the container body to seal the container proximally, and wherein, in a pre-expelling state, a proximally facing surface of the piston assumes an axial start position relative to the proximally facing rim surface, a plunger arranged along the axis and extending from a proximal end to a distal end, the distal end being configured for cooperating with the proximally facing surface of the piston for driving the piston distally relative to the proximally facing rim surface, wherein the plunger comprises a fixed stop surface arranged between the distal end and the proximal end of the plunger, the fixed stop surface being arranged to cooperate with the proximally facing rim surface of the container to define a stop limit for the distal movement of the plunger relative to the proximally facing rim surface, and an expelling mechanism comprising an actuator configured for, upon activation, exerting a distally directed force on the plunger for expelling the dose of the medicament, wherein the container, the plunger and the expelling mechanism are accommodated non-removably relative to the housing, and wherein one or more tolerance compensating elements are arranged:

a) axially between the proximally facing rim surface of the container and the distally facing stop surface of the plunger, and/or b) axially between the distal end of the plunger and the proximally facing surface of the piston, and wherein said one or more tolerance compensating elements are selected from a group of tolerance compensating elements and arranged to compensate for tolerance variations on the axial start position of the proximally facing surface of the piston relative to the proximally facing rim surface.

In one embodiment, the group of tolerance compensating elements defines a first group consisting of a plurality of tolerance compensating elements having different respective axial sizes and each configured for being arranged axially between the proximally facing rim surface of the container and the distally facing stop surface of the plunger.

In a further embodiment, the group of tolerance compensating elements defines a second group consisting of a plurality of tolerance compensating elements having different respective axial sizes and each configured for being arranged axially between the distal end of the plunger and the proximally facing surface of the piston.

In a still further embodiment, the group of tolerance compensating elements contains the tolerance compensating elements of said first group and said second group.

In a still further embodiment, the group of tolerance compensating elements defines:

at least one tolerance compensating element of a pre-defined axial size and configured for being arranged axially between the proximally facing rim surface of the container and the distally facing stop surface of the plunger, and at least one tolerance compensating element of a pre-defined axial size and configured for being arranged axially between the distal end of the plunger and the proximally facing surface of the piston.

In accordance with all the above aspects and embodiments of the invention, the tolerance compensating element or the group of tolerance compensating elements may be configured to compensate for a tolerance variations on the axial start position of the proximally facing surface of the piston relative to the proximally facing rim surface of the cartridge in the order of ±0.5 mm, or, in further embodiments, in the order of ±1.0 mm.

As used herein, the term "medicament" is meant to encompass any drug-containing flowable medicine capable of being passed through a delivery means such as a cannula or hollow needle in a controlled manner, such as a liquid, solution, gel or fine suspension.

BRIEF DESCRIPTION OF DRAWINGS

In the following the invention will be further described with reference to the drawings, wherein FIG. 2 shows a cross sectional side view of a first embodiment of a plunger assembly according to the invention with the plunger assuming a start position, FIG. 3 shows a perspective view of a tolerance compensating element of the plunger assembly shown in FIG. 2, FIG. 4 shows a cross sectional axial view in distal direction through the tolerance compensating element of the plunger assembly shown in FIG. 2.

Figure 1A:
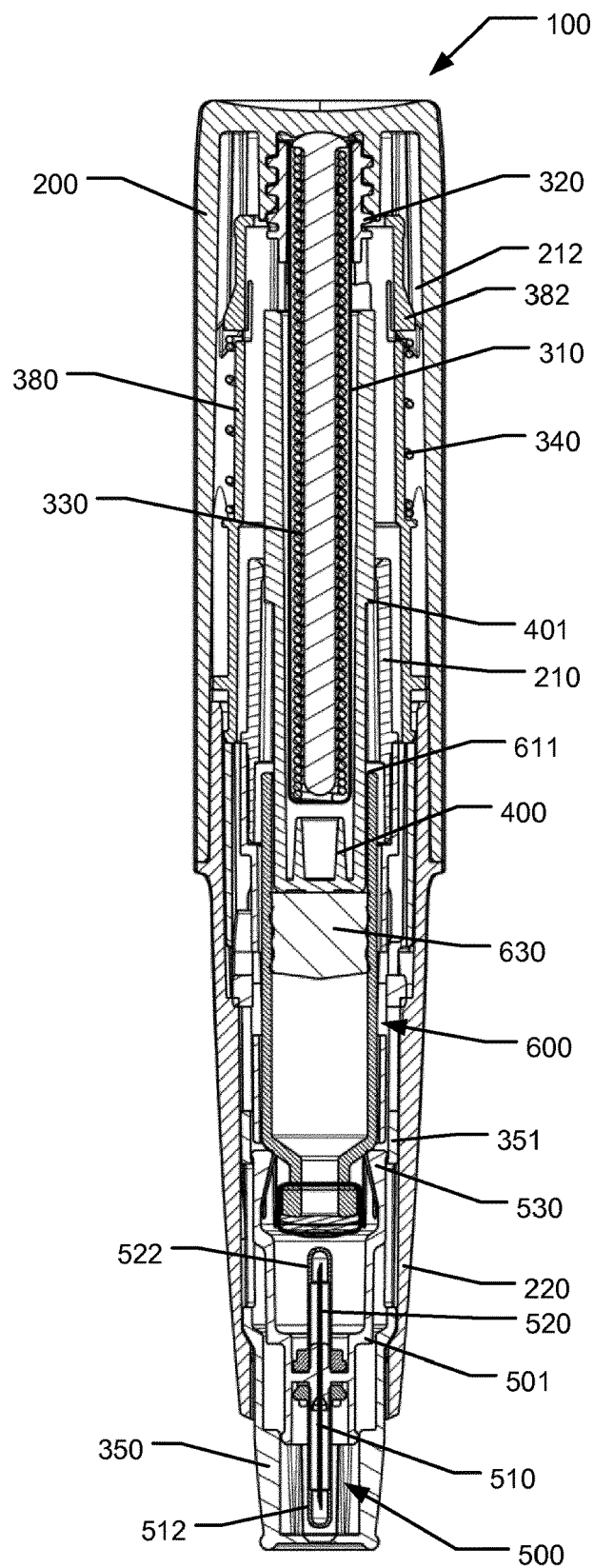
FIG. 1a shows a cross sectional side view of an exemplary injection device which is applicable for use in connection with the present invention, wherein the device is in a state prior to triggering.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DESCRIPTION

Figure 1B:
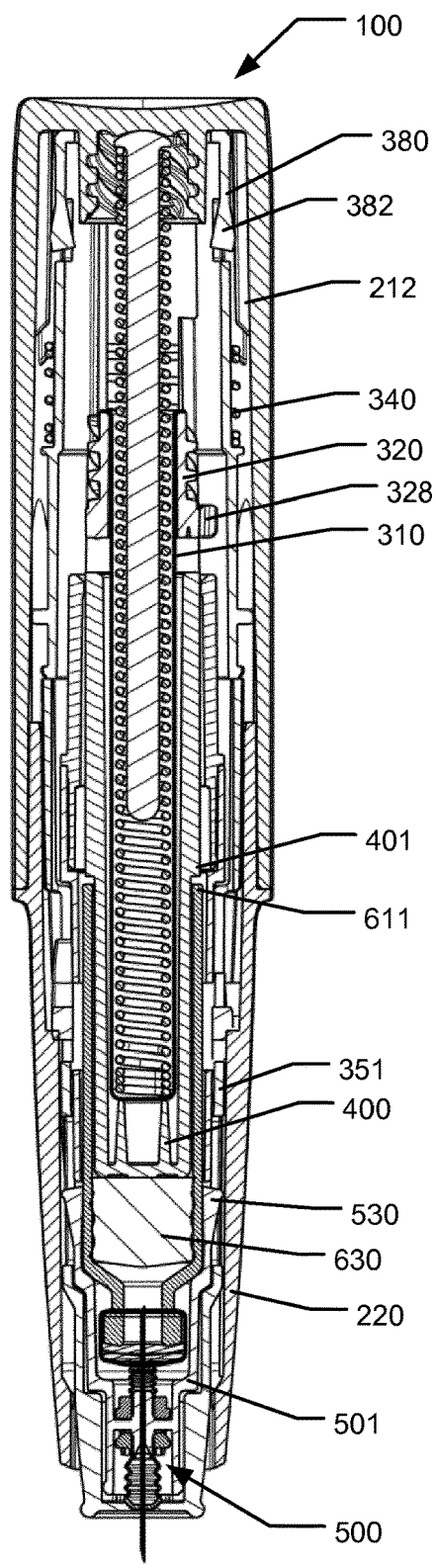
FIG. 1b shows a cross sectional side view of the injection device of FIG. 1a but in a state subsequent to triggering and wherein the device assumes an end of dose state.

FIGS. 1a and 1b illustrate two operational states for an example injection device which is suitable for use in connection with the present invention. The injection device is shown in two different states of operation in order to explain functionality relating to the amount that will be expelled when the injection device is activated for dose expelling. The shown device is generally similar to the device disclosed in WO 2016/075254 A1 in connection with FIGS. 1c, 2c, 3c, 4a, 4b and 5c of said document. FIGS. 1a and 1b of the present disclosure correspond to FIG. 1c respectively FIG. 4b of the WO document. For a detailed description of the disclosed device reference is made to the WO document.

It is to be noted that the shown injection device forms a suitable but non-limiting example and that the principles of the present invention regarding adjusting the dosage amount can be used together with other types of injection devices. All the details of the shown injection device will not be described in detail herein since these details have already been described in the above WO document.

FIGS. 1a and 1b show an injection device 100 in the form of a single use prefilled autoinjector with a medicament containing cartridge 600 irreplaceably accommodated in a housing 200,210,220. The injection device 100 further includes an injection needle assembly 500 having a proximal needle end 520 and a distal needle end 510, a needle shield 350 and an expelling assembly or mechanism which primarily consist of an actuator in the form of a drive ram 310 and a compression spring 330 which provides a plunging force acting on a plunger in the form of ram spacer member 400. The expelling assembly is activatable by means of needle shield 350 so that pushing in of the needle shield 350 relative to the housing triggers the expelling assembly for initiating the expelling action.

In the shown embodiment, in the initial shielded state shown in FIG. 1a, the injection device assumes a state before triggering of the expelling assembly. In the shown embodiment, the container 600 forms a cartridge with a cylindrical body having a distally arranged outlet covered by a cartridge septum adapted to be pierced by the needle for establishing fluid communication with the cartridge interior. The body of the cartridge accommodates a slidably arranged piston 630. In the state where the needle has pierced cartridge septum, piston 630 is drivable towards the outlet in order to dispense medicament from the cartridge 600.

The ram spacer member 400 is formed with stop surfaces 401 positioned a predetermined distance from the distal end of ram spacer member 400 to cooperate with the rear end 611 of the body of cartridge 600 to thereby define a precise end of stroke position for the piston 630 inside cartridge 600. As the piston 630, during filling of the cartridge 600, can be positioned with respect to the rear end 611 of the cartridge 600 in accordance with the desired fill level of the cartridge, the exact volume of an expelled dose can be controlled by utilizing the stop surfaces 401 hitting the rear end 611 of cartridge 600 at completion of the expelling operation. In the shown embodiment, the ram spacer member 400 includes two longitudinally extending ribs positioned 180 deg. apart. Each longitudinally extending rib has a distal end surface which forms said stop surface 401. In the shown embodiment, the ram spacer member 400 is mounted rotationally fixed in the housing of the injection device 100.

Subsequent to triggering and injection, as shown in FIG. 1b, the injection device 100 assumes the end of dose state, but prior to removal of the device from the injection site. The expelling assembly has pushed the piston 630 of the cartridge distally, thereby causing the intended dose of the medicament in the cartridge to be expelled through the needle into the injection site. The stop surfaces 401 of ram spacer member 400 engage the rear end 611 of cartridge 600 thereby controlling the end position of ram spacer member 400 relative to the cartridge 600. Hence, the axial position of the proximal surface of piston 630 corresponds to the axial position of the distal face of the ram spacer member 400.

After the medicament has been injected, the needle shield 350 is again pushed forward with respect to the housing to shield the distal end of the needle. In the shown embodiment, this occurs as a consequence of the user manually retracting the housing of the injection device relative to the injection site. In the shown embodiment, the needle shield 350 is biased in the distal direction by means of a needle shield spring, and the needle shield thus moves automatically into the shielding state wherein the needle shield is permanently locked. The device is then ready to be disposed of.

The description above with respect to FIGS. 1a and 1b has been provided to give background information on the use of an exemplary injection device applicable for use with the present invention. However, the injection device described is one of many different available injection devices that can be utilized with the principles according to the present invention.

In large scale manufacturing, for particular applications such as in connection with treatment with particular kinds of medicaments, the accuracy of the expelled dose from an injection device, such as the one described above, cannot be met with typical predefined tolerance levels. In particular, the initial axial position of the piston relative to the rear surface of the cartridge body may vary, such as in the order of ±0.5 mm, or even ±1.0 mm. In the following, different embodiments will be described which relate to principles that can be used to compensate for such tolerance variations. Utilizing these principles, the accuracy of expelling a single dose from a cartridge can be increased thereby providing an improved injection device.

FIG. 2 shows a first embodiment of a plunger assembly 10.1 according to the invention. Plunger assembly 10.1 includes a cartridge 60, a plunger 40 and a tolerance compensating element 70. The plunger assembly 10.1 is intended to replace the ram spacer member 400 and the cartridge 600 in the above described injection device 100.

Cartridge 60 is similar to cartridge 600 referred to above. Cartridge 600 comprises a cylindrical body 61 within which a slideable piston 63 is arranged at a particular initial axial location with respect to a proximally facing rim surface 64 of body 61.

Plunger 40 performs the same function as ram spacer member 400 described above. Plunger 40 forms an elongated generally tubular element configured to be partially inserted axially into the body of the cartridge. In the shown embodiment, plunger 400 is formed with two radially opposed longitudinal extending ribs 45. Each of the longitudinal extending ribs 45 ends in a distally facing stop surface 46 which in this disclosure also will be referred to as "a counter stop surface". The distally facing stop surfaces 46 are positioned at a predefined axial distance from a distal end face 41 of plunger 40 in order to cooperate, via tolerance compensating element 70, with the proximally facing rim surface 64 of cartridge 60.

The tolerance compensating element 70 is better viewed in FIG. 3. In the first embodiment, the tolerance compensating element 70 is formed as a collar to be arranged circumferentially relative to the plunger 40 and with a distal annular face 74 dimensioned to engage and lie flush against the proximally facing surface 64 of cartridge 60. The proximal facing surface 76 of tolerance compensating element 70 is formed with a contour system comprising a plurality of circumferentially disposed stop surfaces 76.1-76.13 being arranged axially offset relative to each other. In the shown embodiment the contour system is formed with a plurality of steps that are circumferentially arranged and axially offset relative to one another. In the shown embodiment, two sets of contour systems are arranged opposing each other. In each contour system 13 individual steps are formed in a series of steps 76.1-76.13 covering an angle of 180 degrees. The 13 individual steps are thus repeated twice on the circumference so that each step at a particular axial position finds a counterpart separated by 180 degrees but arranged at the same axial level.

On the radially inwards facing surface of tolerance compensating element 70 a series of axially extending grooves 73 is arranged circumferentially to cooperate with one or more axially extending tongues 43 formed to protrude radially outwards from plunger 40. In an initial assembly configuration, before assembling the plunger 40 relative to the tolerance compensating element 70, a particular rotational orientation between the two components may be selected whereafter, when the plunger 40 is inserted into the tolerance compensating element 70, the two components becomes rotationally fixed relative to each other. The tongue and groove system 43/73 is formed so that the plunger 40 is freely axially slidable relative to the tolerance compensating element 70 even when the two components are rotationally fixed relative to each other. As an alternative to the shown rotational locking engagement, a rotational snap engagement may be provided forming a rotational detent mechanism which serves to enable rotational adjustment during assembly operations but to lock the two components to each other to prevent unintentional rotational movement after final assembly.

Figure 6:
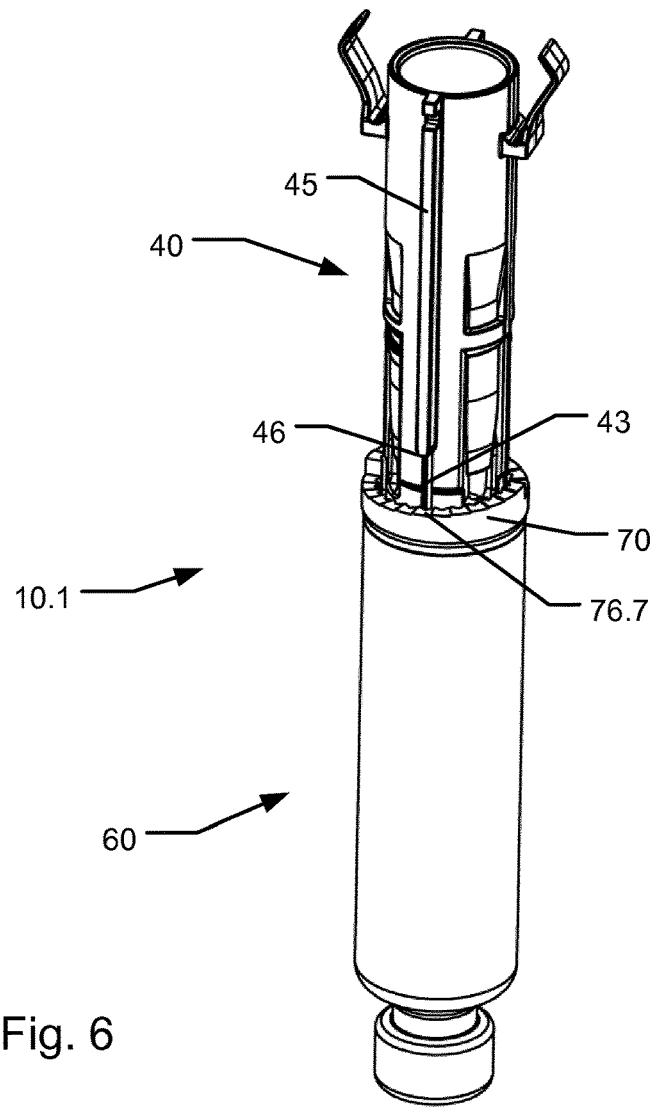
FIG. 6 shows a perspective view of the plunger assembly shown in FIG. 2 with the plunger in the start position.
Figure 7:
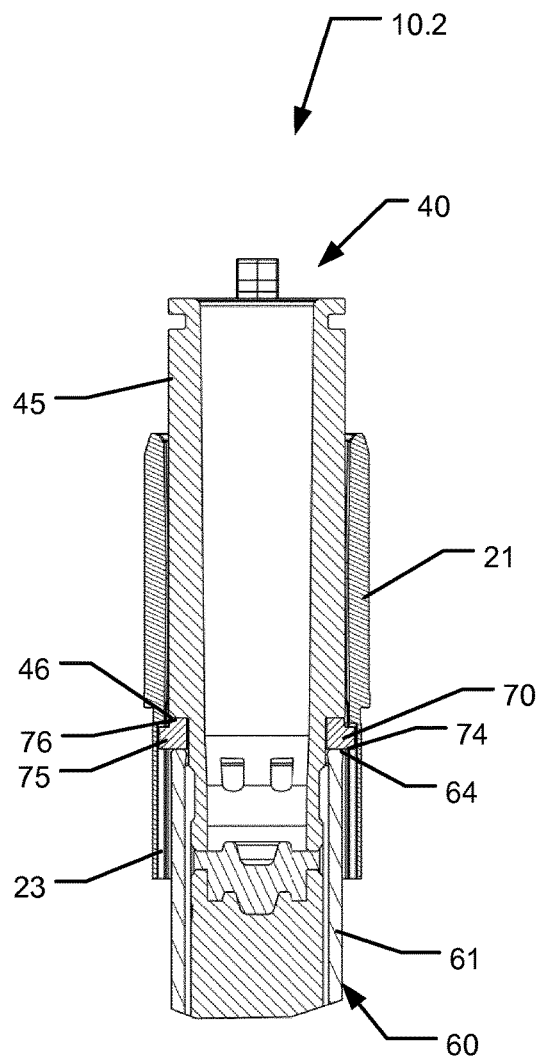
FIG. 7 shows a cross sectional side view of a second embodiment of a plunger assembly according to the invention with the plunger assuming an end position.

In a final assembly configuration, as shown in FIGS. 2 and 6, in accordance with the particular selected rotational position of the tolerance compensating element 70 relative to the plunger 40, the counter stop surfaces 46 and the selected ones of the circumferentially arranged radial steps 76.1-76.13 are rotationally aligned relative to each other, enabling said counter stop surfaces to axially abut respective selected ones of the circumferentially disposed steps to thereby control the end position of the plunger 40 relative to the proximally facing rim surface 64 of the container 60. In the shown example each of the counter stop surfaces 46 is aligned with a stop surface 76.7 on the tolerance compensating element 70.

Figure 5:
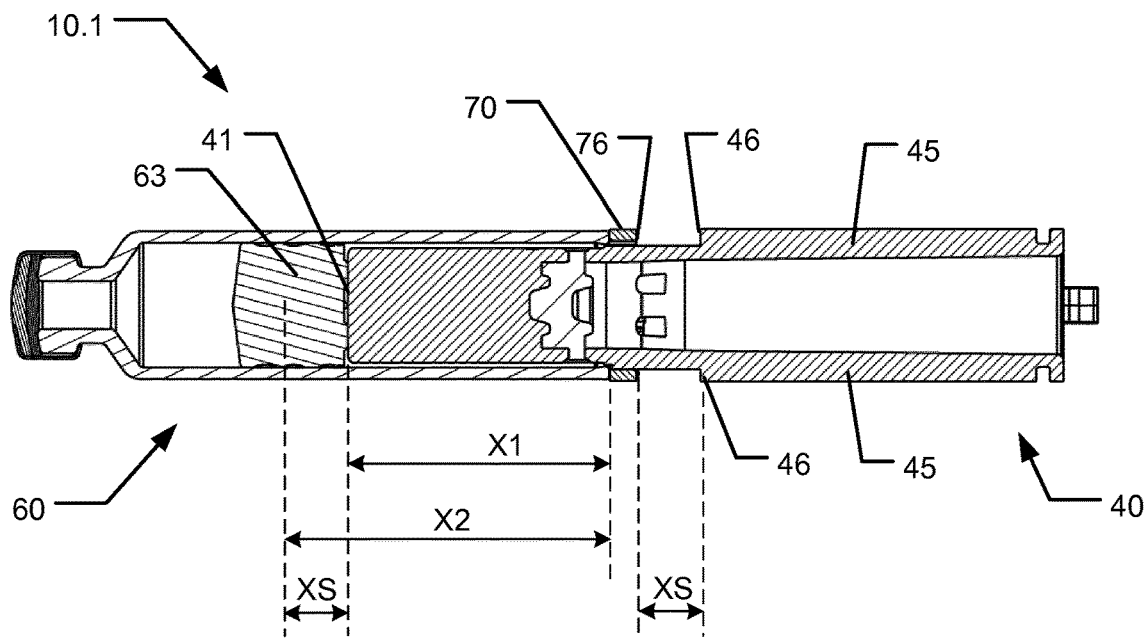
FIG. 5 shows a view similar to the view of FIG. 2 with additional information relating to the expellable amount of medicament from the cartridge.

Referring to FIG. 5, during assembly operations of a particular plunger assembly 10.1, the initial axial position ($X_1$) of the piston 63 with respect to the proximally facing rim surface 64 of the cartridge body 61 may be determined by means of a measuring probe, by way of optical measurements, or by alternative suitable measuring methods. In accordance with the measured information, a particular rotational orientation may be selected between the plunger 40 and the tolerance compensating element 70. Said selection is performed, preferably in an automated manufacturing setup, to ensure that the axial stroke of the piston 63 relative to the cartridge body 61, as driven distally by the plunger 40 during a subsequent expelling procedure, is within a target axial stroke ($X_s$). When the desired amount has been expelled, i.e. with the piston 63 assuming the end of dose position, the piston is located at position ($X_2$) with respect to the proximally facing rim surface 64 of the cartridge body 61. Generally, when referring to the proximally facing rim surface 64 of the cartridge body 61, the distance $X_2$ equals $X_1+X_s$. Generally, when the plunger sub-assembly is formed, e.g. when the medicament injector is assembled, the plunger will typically not assume a position where full engagement between the plunger and the piston is obtained. However, during expelling, after an initial movement of the plunger, the plunger reaches an axial position where it engages the piston and the final stroke of the plunger $X_s$ generally corresponds to target axial stroke $X_s$ of the piston.

The plunger assembly, in its final assembly configuration with the tolerance compensating element properly adjusted, can be assembled with the remaining components of an injection device. Preferably, the plunger assembly is received within housing components that are permanently attached relative to each other so as to render further adjustments impossible between the plunger and the tolerance compensating element. In the described manner, the tolerance variations of the individual components of the device, and the tolerance induced variations on the accuracy of the size of the expelled dose of medicament from the device, can be effectively eliminated.

It is to be noted that, in other alternative embodiments, the number of counter stop surfaces may be lower or higher than two. Similarly, instead of forming the contour system as two repeated series of steps, only a single or more than two series may be formed on the tolerance compensating element. The number of steps of each contour system may also be varied, such as incorporating only a limited number of axial positions, such as only two, three, four or more steps with a corresponding number of unique axial positions. In still other embodiments where the tolerance compensating element comprises one or more contour systems, a plurality of counter stop surfaces may be designed on the plunger as a separate contour system to cooperate with the contour system of the tolerance compensating element. It is to be noted that, even though the shown contour system comprises steps that are arranged along a helical path on the plunger, the contour system need not be arranged along a helical pat but could be formed along differently formed paths.

It is also to be noted that, in other alternative embodiments, the contour system may alternatively be formed onto the plunger whereas the counter stop surfaces may be provided on the tolerance compensating element. Further, instead of the tolerance compensating element being arranged to constantly engage the proximally facing rim surface of the container, the tolerance compensating element may be arranged to travel with the plunger as the plunger moves axially relative to the cartridge. In such system, the end position of the plunger is assumed when the distal face 74 of the tolerance compensating element hits the proximally facing rim surface 64.

FIGS. 7-11 show a second embodiment of a plunger assembly 10.2 which is formed generally corresponding with the plunger assembly 10.1 of the first embodiment. However, instead of forming a rotational tongue and groove system between the plunger and the tolerance compensating element 70, the tolerance compensating element is, in an adjustable manner, rotationally aligned and subsequently locked relative to a housing component 21. Such housing component may be formed generally similar to housing component 210 of the injection device 100 shown in FIGS. 1a and 1b. To improve clarity the housing component 21 is omitted from view in FIGS. 9-11. For some embodiments, in a particular assembly state during manufacturing of a pre-filled medicament injector, the housing component 21 may form part of the plunger assembly 10.2.

Figure 8:
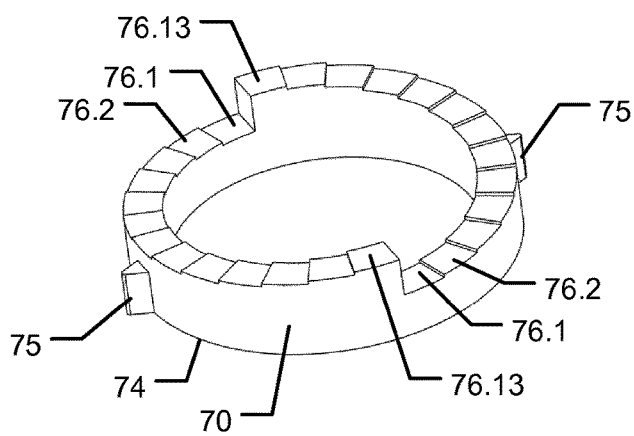
FIG. 8 shows a perspective view of a tolerance compensating element of the plunger assembly shown in FIG. 7.
Figure 9:
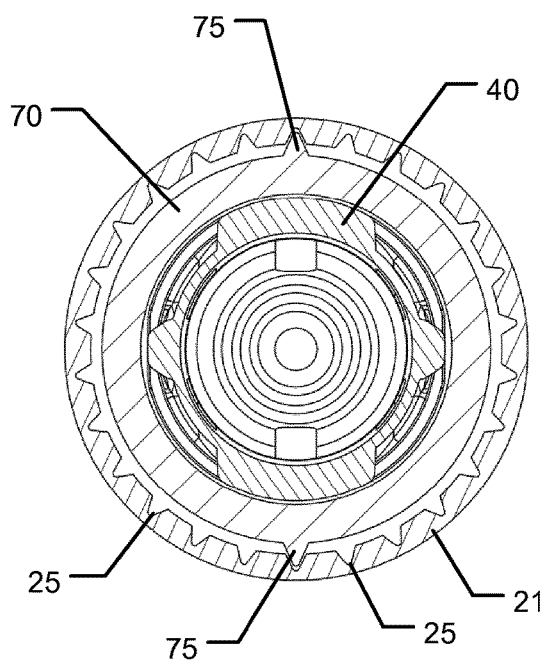
FIG. 9 shows a cross sectional axial view in distal direction through the tolerance compensating element of the plunger assembly shown in FIG. 7.
Figure 10:
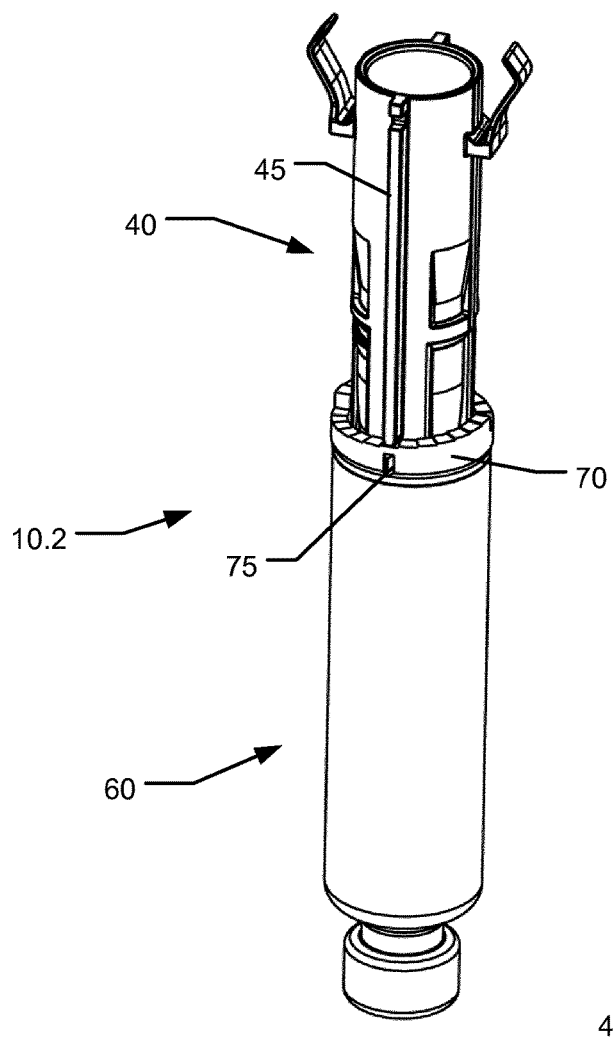
FIG. 10 shows a perspective view of the plunger assembly shown in FIG. 7 with the plunger in the end position.
Figure 11:
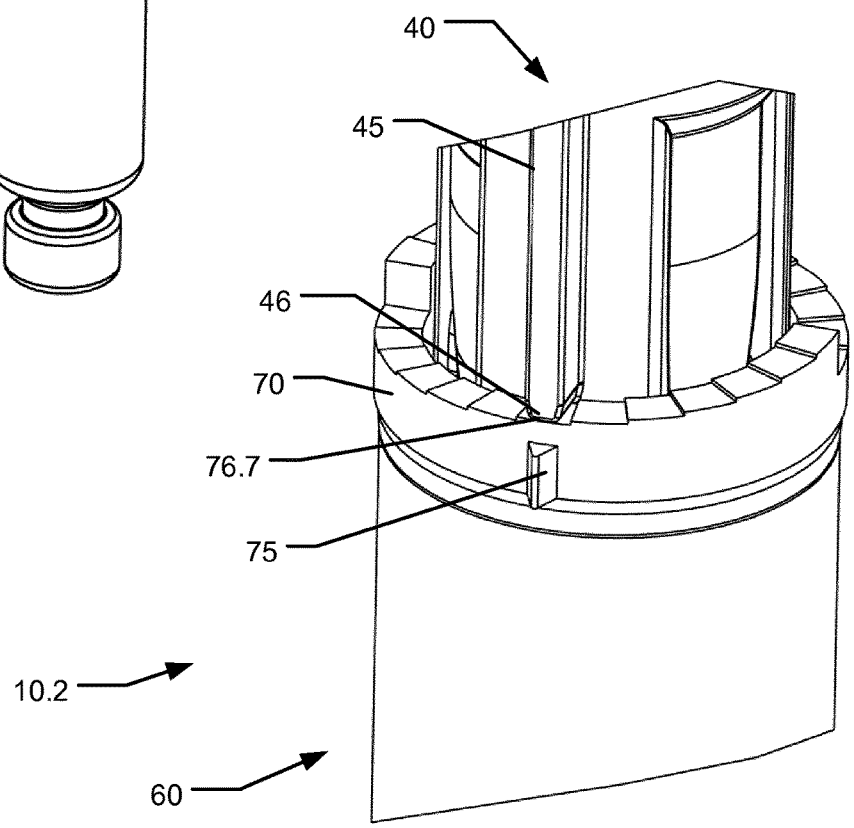
FIG. 11 shows a magnified view of the part of FIG. 10 showing the tolerance compensating element.

As shown in FIGS. 8, 9 and 10, two tongues 75 are formed to protrude radially outwards from the outer surface of tolerance compensating element 70. Each tongue 73 is arranged to cooperate with a selected one of a plurality of axially extending grooves 23 formed circumferentially on a radially inwards facing surface in housing component 21. In an initial 75 assembly configuration, before assembling tolerance compensating element 70 relative to the housing component 21, a particular rotational orientation between the two components may be selected. Hereafter, when the tolerance compensating element 70 is inserted into the housing component 21, the two components becomes rotationally fixed relative to each other.

The plunger assembly 10.2, in its final assembly configuration, can be subsequently assembled with the remaining components of an injection device to form a pre-filled injection device having superior dosage accuracy.

Figure 12:
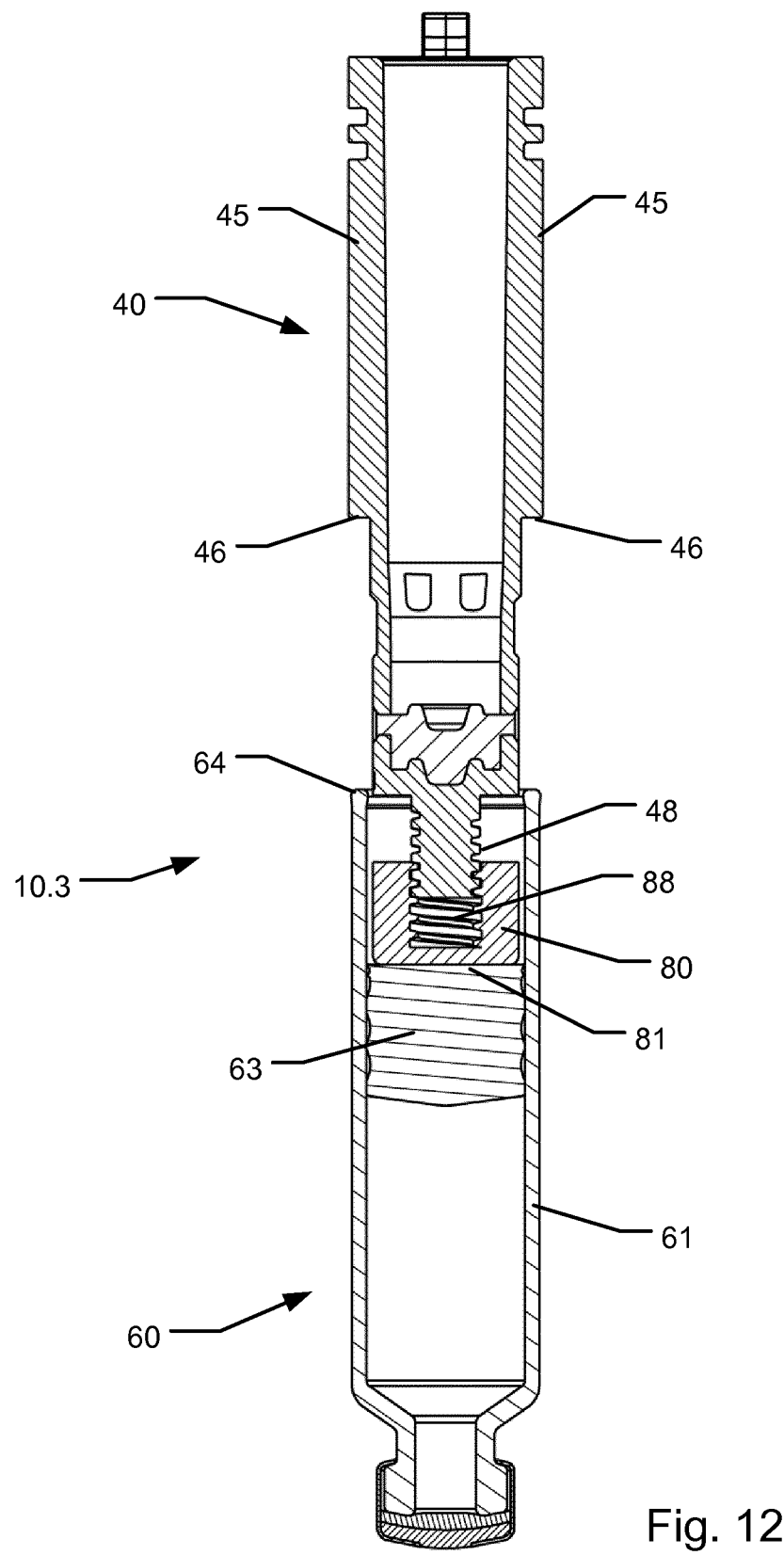
FIG. 12 shows a cross sectional side view of a third embodiment of a plunger assembly according to the invention with the plunger assuming a start position.

Finally, turning to FIG. 12, a third embodiment of a plunger assembly 10.3 according to the invention is showed. Plunger assembly 10.3 includes a plunger which forms two distally facing counter stop surfaces 46 configured to engage directly with the proximally facing rim surface 64 of the cartridge body 61. In this embodiment, the plunger connects to the piston 63 of the cartridge via a tolerance compensating element 80 connected to a distal end of the plunger 40. Tolerance compensating element 80 comprises a distally facing surface 81 configured for engaging directly with the distal surface of the piston 63. Tolerance compensating element 80 further comprises a proximally facing bore provided with a thread 88. The distal end of plunger 40 is formed with a corresponding external thread 48 that is in engagement with the thread 88 of tolerance compensating element 80.

By rotating the tolerance compensating element 80 and the plunger 40 relative to each other the effective axial distance between the distally facing surface 81 of tolerance compensating element 80 and the counter stop surfaces 46 can be selected in accordance with a measured axial position of the piston 63 relative to the proximally facing rim surface 64 of the cartridge body 61. The measurement may be performed by using the same means and methods as described above with respect to plunger assembly 10.1. The threaded engagement 88/48 is preferably formed as a self-locking threaded connection, meaning that the threaded engagement is configured to inhibit self-induced rotation when the plunger 40 exerts an axial force via the tolerance compensating element 80 onto the proximal face of the piston 63. Preferably, the friction between the threads 88 and 48 is designed with a magnitude so that rotation is exclusively performed when a suitable tool is exerting a torque between the plunger 40 and the tolerance compensating element 80.

The plunger assembly 10.3, in its final assembly configuration, just as with the plunger assemblies 10.1 and 10.2 described above, can be subsequently assembled with the remaining components of an injection device. Preferably, the plunger assembly 10.3 is received within housing components that are permanently attached relative to each other so as to render further adjustments impossible between the plunger and the tolerance compensating element. In the described manner, the tolerance variations of the individual components of the device, and the tolerance induced variations on the accuracy of the size of the expelled dose of medicament from the device, can be effectively eliminated.

Some preferred embodiments have been shown in the foregoing, but it should be stressed that the invention is not limited to these, but may be embodied in other ways within the subject matter defined in the following claims and within the remaining disclosure.

The invention claimed is:

1. A plunger sub-assembly for a pre-filled medicament injector for expelling a dose of a medicament, comprising:
   a container holding a medicament, the container comprising a cylindrical container body extending along a central axis between a medicament expelling distal end and a proximal end, wherein an axially slideable piston is arranged within the container body to seal the container proximally, and wherein the proximal end of the container body comprises a proximally facing rim surface,
   a plunger arranged along the axis and configured for driving the piston distally relative to the proximally facing rim surface, the plunger being distally movable from a start position where the plunger is not cooperating with the proximally facing rim surface until an end position relative to the container where the plunger cooperates with the proximally facing rim surface thereby preventing the plunger from moving further distally, the piston assuming an end of dose position relative to the proximally facing rim surface when the plunger assumes the end position, and
   an adjustable blocking structure associated with the plunger and the container to provide an axial blocking structure for the plunger in the end position,
wherein the adjustable blocking structure comprises a tolerance compensating element configured to cooperate with the plunger and to cooperate with the proximally facing rim surface, wherein the tolerance compensating element is rotatable relative to the plunger to adjust the piston end of dose position relative to the proximally facing rim surface, wherein the tolerance compensating element is so configured that, when the plunger assumes the end position,
the plunger engages directly with the piston, whereas the tolerance compensating element directly engages both the plunger and the proximally facing rim surface
wherein one of the plunger and the tolerance compensating element comprises a contour system comprising a plurality of circumferentially disposed stop surfaces that are arranged axially offset relative to each other, and wherein the other of the plunger and the tolerance compensating element comprises a counter stop surface arranged to axially engage a selective one of the plurality of circumferentially stop surfaces, and
wherein, when in an initial assembly configuration, the tolerance compensating element and the plunger are positioned relative to each other to rotationally align the counter stop surface with a selective one of the plurality of circumferentially disposed stop surfaces to thereby adjustably control the end position of the plunger relative to the container, enabling the counter stop surface to axially abut the selected one of the plurality of circumferentially disposed stop surfaces.

2. The plunger sub-assembly as defined in claim 1, wherein, when the plunger assumes the end position, a distally facing geometry of the plunger engages directly with the piston, whereas the tolerance compensating element directly engages both the plunger and the proximally facing rim surface, and wherein the tolerance compensating element is formed as a collar arranged circumferentially relative to the plunger and having a distal annular surface, the distal annular surface configured for engaging the proximally facing rim surface.

3. The plunger sub-assembly as defined in claim 1, wherein the plurality of circumferentially disposed stop surfaces of the contour system define a plurality of steps that are circumferentially arranged and axially offset relative to one another.

4. The plunger sub-assembly as defined in claim 1, wherein, in a final assembly configuration, the tolerance compensating element and the plunger are positioned rotationally locked relative to each other with rotational alignment of the counter stop surface with the selected one of the plurality of circumferentially disposed stop surfaces, causing said counter stop surface to axially abut said selected one of the plurality of circumferentially disposed stop surfaces to thereby control the end position of the plunger relative to the container body.

5. The plunger sub-assembly as defined in claim 1, wherein the plunger and the tolerance compensating element engage with each other by structure of a tongue and groove system, the tongue and groove system defining at least one tongue and a plurality of axially extending grooves disposed in a coaxial configuration, wherein the tongue positioned in a selective one of said plurality of axially extending grooves to rotationally align said counter stop surface with the selected one of the plurality of circumferentially disposed stop surfaces enabling an axially sliding movement of the plunger and the tolerance compensating element relative to each other while preventing relative rotational movement there between.

6. The plunger sub-assembly as defined in claim 1, wherein the injector defines a base component that is mounted axially fixed relative to the container body and that partially or fully encircles the plunger, wherein the plunger and the base component are mounted non-rotatably relative to each other, wherein the base component and the tolerance compensating element engage with each other by structure of a tongue and groove system, the tongue and groove system defining at least one tongue and a plurality of axially extending grooves disposed in a coaxial configuration, and wherein the tongue positioned in a selective one of said plurality of axially extending grooves to rotationally align said counter stop surface with the selected one of the plurality of circumferentially disposed stop surfaces to prevent relative rotation between the base component and the tolerance compensating element.

7. The plunger sub-assembly as defined in claim 1, wherein said counter stop surface and additional corresponding counter stop surfaces are provided as a plurality of circumferentially disposed counter stop surfaces distributed regularly around the central axis, wherein the respective ones of the plurality of circumferentially disposed counter stop surfaces are configured for simultaneously axially engaging a respective one of the plurality of circumferentially disposed stop surfaces.

8. The plunger sub-assembly as defined in claim 5, wherein the groove and tongue comprise engaging surfaces being so configured that the tolerance compensating element and the plunger is selectively rotationally positionable relative to each other in incremental angular steps having a step size between 5 and 180 Deg.

9. The plunger sub-assembly as defined in claim 1, wherein the plunger and the tolerance compensating element, in a final assembly configuration, are prevented from rotating relative to each other by structure of a rotational lock.

10. A pre-filled medicament injector for expelling a dose of a medicament, comprising:
   a housing comprising first and second housing components,
   the plunger sub-assembly as defined in claim 1, and
   an expelling mechanism comprising an actuator configured for, upon activation, exerting a distally directed force on the plunger for expelling the dose of the medicament,
wherein the plunger sub-assembly and the expelling mechanism are accommodated non-removably relative to the first and second housing components.

11. The pre-filled medicament injector as defined in claim 10,
   wherein the tolerance compensating element and the plunger are positioned relative to each other providing a permanent rotational alignment between the counter stop surface and a selected one of the plurality of circumferentially disposed stop surfaces, enabling said counter stop surface to axially abut said selected one of the plurality of circumferentially disposed stop surfaces to thereby control the end position of the plunger relative to the container.

12. A method of assembling the pre-filled medicament injector as defined in claim 11, comprising the steps of:
   providing the container,
   determining the axial position ($X_1$) of a proximal face of the piston with respect to the proximally facing rim surface,
   establishing a target axial end of dose position ($X_2$) of the proximal face of the piston with respect to the proximally facing rim surface for obtaining a predetermined target axial stroke ($X_S$) for the piston,
   providing the plunger and the tolerance compensating element,
   based on the target axial end of dose position ($X_2$) of the proximal face of the piston, determining a target axial end position for the distal end face of the plunger,
   based on said target axial end position for the distal end face of the plunger, determining a target stop surface selected from the plurality of circumferentially disposed stop surfaces so that the axial end position of the distal end face of the plunger substantially corresponds to the target axial end of dose position ($X_2$) of the proximal face of the piston when said target stop surface axially abuts the counter stop surface,
   based on the target stop surface, positioning the plunger and the tolerance compensating element with respect to each other so that the target stop surface rotationally aligns with the counter stop surface,
   forming the plunger sub-assembly,
   providing the expelling mechanism and the first and second housing components, and
   permanently attaching the first and the second housing components to each other to form a housing, whereby the plunger sub-assembly and the expelling mechanism are accommodated non-removable relative to the housing.

13. The plunger sub-assembly as defined in claim 8, wherein the angular step size is between 10 and 30 Deg.

14. The plunger sub-assembly as defined in claim 8, wherein the rotational lock is formed by cooperating rigid geometries.

15. The plunger sub-assembly as defined in claim 8, wherein the rotational lock is formed by a rotational detent mechanism.

16. The plunger sub-assembly as defined in claim 1, wherein the container of the plunger sub-assembly defines a cartridge that comprises a septum that seals an expelling distal end of the container body, the septum being penetrable by a needle cannula to establish fluid communication with the interior of the container.

* * * * *